United States Patent
King et al.

(10) Patent No.: US 6,699,657 B2
(45) Date of Patent: Mar. 2, 2004

(54) IN VITRO SYSTEM FOR REPLICATION OF RNA-DEPENDENT RNA POLYMERASE (RDRP) VIRUSES

(75) Inventors: Robert W. King, West Chester, PA (US); Matthew W. Jeffries, Wilmington, DE (US); Claudio Pasquinelli, Media, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/066,130

(22) Filed: Jan. 31, 2002

(65) Prior Publication Data

US 2003/0175683 A1 Sep. 18, 2003

Related U.S. Application Data

(60) Provisional application No. 60/265,437, filed on Jan. 31, 2001.

(51) Int. Cl.$^7$ ............... C12Q 1/25; C12Q 1/20; C12N 7/00; C12N 15/40; C12N 15/51
(52) U.S. Cl. ............ 435/5; 435/7.91; 435/7.21; 435/8; 435/465; 435/235.1; 435/325; 435/69.2; 536/23.1; 536/24.5
(58) Field of Search ............... 435/5, 7.91, 8, 435/7.21, 465, 366, 235.1, 325, 69.2; 536/24.5, 23.1

(56) References Cited

U.S. PATENT DOCUMENTS

| | | | | |
|---|---|---|---|---|
| 5,670,356 A | * | 9/1997 | Sherf et al. | 435/172.3 |
| 6,030,785 A | | 2/2000 | Katze et al. | |
| 6,297,003 B1 | | 10/2001 | Rice et al. | |
| 6,326,480 B1 | * | 12/2001 | Kovelman et al. | 536/23.1 |
| 6,447,994 B1 | * | 9/2002 | Schmidt et al. | 435/5 |

OTHER PUBLICATIONS

Goobar–Larsson et al. Arch Virol. 2001, vol. 146, pp. 1553–1570.*
Bartenschlager and Lohman (2000) J. Gen. Virol. 81, 1631–1648.
Kolykhalov et al. (1997) Science 277, 570–574.
Neuman et al. (1998) Science, 282, 103–107.
Tong et al. (1995) Lancet 345, 1058–1059.
Saito et al. (1990) Proc. Natl. Acad. Sci. USA 87, 6547–6549.
Bartenschlarger et al. (1994) J. Virol. 68, 5045–5055.
Eckart et al. (1993) BBRC 192, 399–406.
Grakoui et al. (1993) J. Virol. 67, 2832–2843.
Lin et al. (1994a) J. Virol. 68, 5063–5073.
Lin et al. (1994b) J. Virol. 68, 8147–8157.
Lohmann V., Korner F., Koch J.O., Herian U., Theilmann L. and Bartenschlager R. (1999) Replication of subgenomic hepatitis C virus RNAs in a hepatoma cell line. Science. 285:110–113.
Ohishi M., Sakisaka S., Harada H., Koga H., Taniguchi E., Kawaguchi T., Sasatomi K., Sata M., Kurohiji T. and Tanikawa K. (1999) Detection of hepatitis–C virus and hepatitis–C virus replication in hepatocellular carcinoma by in situ hybridization. Scandinavian J. Gastroenterology. 34:432–438.
Rijnbrand R.C.A. and Lemon S.M. (2000) Internal ribosomal entry site–mediated translation in hepatitis C virus replication. In, Current Topics in Microbiology and Immunology, Eds. Hagedorn, C.H. and Rice, C.M. pp. 85–116. Springer–Verlag Berlin.

* cited by examiner

*Primary Examiner*—James Housel
*Assistant Examiner*—Bao Qun Li
(74) *Attorney, Agent, or Firm*—John A. Lamerdin

(57) ABSTRACT

An in vitro method to conduct genomic replication of the viral genomes of viruses that utilize RNA-dependent RNA polymerase for replication (RDRP viruses), such as HCV. The method employs a construct comprising the 3' and 5' untranslated regions (UTRs) of the viral genome which are operably linked on the 5' and 3' ends of a reporter sequence, in antisense orientation, such that when viral replication is occurring within the cell which produces RDRP, the reporter protein will be made. The method of the invention provides an efficient means for measuring genomic replication in RDRP viruses, and also for the rapid screening of compounds for their ability to inhibit genomic replication of RDRP viruses, including the Hepatitis C virus (HCV).

11 Claims, 8 Drawing Sheets

Nucleotide Sequence of pMJ050

SEQ ID NO:17 is nucleic acids 1-5860
SEQ ID NO:18 is nucleic acids 1-2771
SEQ ID NO:19 is nucleic acids 1-2674
SEQ ID NO:20 is nucleic acids 348-2674

SV40 promoter sequence

1...ggatccgctgtggaatgtgtgtcagttagggtgtggaaagtccccaggctccccagcaggcagaagtatgcaaagcatgcatctcaattagtcagcaaccaggtgtggaa
agtccccaggctccccagcaggcagaagtatgcaaagcatgcatctcaattagtcagcaaccatagtcccgcccctaactccgcccatcccgcccctaactccgcccagttccg
cccattctccgccccatggctgactaattttttttatttatgcagaggccgaggccgcctcggcctctgagctattccagaagtagtgaggaggcttttttggaggcctaggctttgc
aaaa...347

3'UTR sequence (antisense)

348...agcttacatgatctgcagagagccagtatcagcactctctgcagtcatgcggctcacgactagccgctaggcctgactaggcctgactaggcctgactaggcctgactaggcctgactagg
taaagaaggaaggaaggaaagaaagaaagaaaagaaagaaagaaaagaaagaaagaaaagaaagaaagaaaagaaagaaaaaaaaaaaaaaa
aaaaaaaaaaaaaaaaaaaaaaaaacaggaaatggcctaagagaggccggagtgtttaccccaacctta...626

Numbers before and after each individual sequence refers to the base number in plasmid, pMJ050. To assemble the nucleotide sequence of pMJ050 as a whole, each individual sequence can be ordered numerically, starting with the SV40 promoter sequence.

FIG. 3A

Luciferase sequence (antisense)

627...aacggcgatctttccgcctcttggcctttcttgaggatctctctgattttcttggtcgagttttcggtacttcgtccacaaacacaactcctccgcg
caacttttcgcgggttgttacttgactggcgacgtaatccacgatctctttttccgtcatcgtcttccgtgctcccaaacaacacggcgggaagttcacggcgtcat
cgtcgggaagacctgcgaacctgcgtcgaagatgttgggcgtgagcaagatggattccaattcagcgggagccacctgatagccttttgtacttaatcagagacttc
aggcggtcaacgatgaagaagtgttcgtcttcgtcccagtaagctatgtccagaatgctagcaccatccttgtcaatcaggcgttggtcgcttccggattgttttacata
accggcataatcatagaagaccctcacacacagttcgctctcttgattaacgccagcgtttcccggtataccagatcccaccttgcctgatacctggcagatggaacctcttggcaacgct
cgaccgcgccggttttatcatccccctcggtgtaatcagaattcgtgatgtagttcgtcagtgagcccatatccttgcctgagagtcgtatttgtcaatcagagtgcttttggcgaagaagaagatccgagtgttggca
tccccgactcctttagagaggggagcgcccagaaggctcctgtaatcctgaaggctccctgaaggctccacactcttcttcaaatctataacattaagacgactcgaaatccacatatcaaatatccgagtgtagtaa
ccagcagcgacttttgaatcttgtaaccgtgaatggaacaacacttaaaatcgcagtatccggaatgattcgattcagtgcaattgctttgtccctatcgaaatcgacaaaatctcacgcaggcagttc
acattccaaaaccgtgatggagcgacaccttaggcagacgacgtgtgacgaagcatcatcgactagatcatcgagagtacatccctgctgaaatcccggtatccctcgtttagaatccatgatcagtgcaattcacgttcattaaatgtcgttcgcgggcgcaactgcaa
tatgaggcagacgcacccttaggcagacgacgtgtgacgaagctagatcatcgacagtgtcagtgtacatccgctgcgaaatccctggtgcgaaatgccatactgttgagcaattcacgtcattaaatgtcgttcgcgggcgcaactgcaa
accgggaggtagatgagatggacgaaccccttttgcaacgcccaacacggccatagaagaattgaagagatgttgagcatatcagatccgagatagatcctgcatatgtgccagaattctgtgattgtattcagccctatatcgtttcaggaaccaggggtgtatctctttcatgcgctatgcagttgctc
caaatttttgcaacccctttgaaacgaacaaccacggcataaagaattgaagagatgttgagcatatcagatccgagatagatcctgcatatgtgccagaattctgtgattgtattcagccctatatcgtttcaggaaccaggggtgtatctctttcatgcgctatgcagttgctc
ctccgataaataacgcccaacacggccataagtcatcagcgtaagtgatgcgccgggatagaatggcgcgggcctttctttatgttttttggcgtcttccatgggacgtc...2284
gaacggacatttccatCttccagcggataagaatggcgcgggcctttctttatgttttttggcgtcttccatgggacgtc...2284
tccagcggttccatCttccagcggataagaatggcgcgggcctttctttatgttttttggcgtcttccatgggacgtc...2284

5'UTR sequence (antisense)

2285...ggttggtgttacgtttggttttctttgaggtttaggattcgtgctcatgatgcacgtctacgagacctccggggcactcgcaagcacccctatcaggcagta
ccacaaggcctttcgcgacccaacactcggctagcagtcttgcgggggcacgcccaaatctccaggcattgagcggggttatccaagaaaggaccggtcgtc
ctggcaattccggtgtactcaccggttcctcacaggggagtgattcgtggtggagtgtcgccccatcagggggctggc...2674

Hepatitis delta virus ribozyme sequence (sense)

2675...ggccggcatggtcccagcctcctcgctggcgccggctgggcaacattccgaggggaccgtccccctcggtaatggcgaatgggacccacaaatctctc...2771

FIG. 3B pMJ050 plasmid backbone sequence

2772...tagatacctagtgagctctcgtacctcgagaattcgaacgcgtgatcagctgttcttctatagtgtcacctaaatagcttcgaggtcgacctcgaaacttgtttattgcagc
ttataatggttacaaataaagcaataagcattcacaaatttcacactcgcatcctttttcactgcattcagttgttgttcctcaaactcatcaatgtatcctatcatgtctg
gatccctcggagatctggcctgccatggccgcgggcagcaatccgtcactcaaaggcgttatccacagaatacggttatccatagctccgccctgacgaatcaggggataacgcaggaaagaacatgtgag
caaaaggccagcaaaaggccaggaaccgtaaaaaggccgcgttgctgggcgtttttccataggctccgcccccctgacgagcatcacaaaaatcgacgctcaagtcaga
ggtggcgaaacccgacaggactataaagataccaggcgttcccccctggaagctccctcgtgcgctctcctgttccgaccctgccgcttaccggatacctgtccgcctttct
cccttcgggaagcgtggcgctttctcaatgctcacgctgtaggtatctcagttcggtgtaggtcgttcgctccaagctgggctgtgtgcacgaaccccccgttcagcccgacc
gctgcgccttatccggtaactatcgtcttgagtccaacccggtaagacacgacttatcgccactggcagcagccactggtaacaggattagcagagcgaggtatgtaggc
ggtgctacagagttcttgaagtggtggcctaactacggctacactagaaggacagtatttggtatctgcgctctgctgaagccagttaccttcggaaaaagagttggtagc
tcttgatccggcaaacaaaccaccgctggtagcggtggtttttttgtttgcaagcagcagattacgcgcagaaaaaaaggatctcaagaagatcctttgatcttttctacgg
gtctgacgctcagtggaacgaaaactcacgttaaggattttggtcatgagattatcaaaaaggatcttcacctagatccttttaaattaaaaatgaagttttaaatcaatctaaagtatatatgagtaaacttggtctgacagttaccaatgcttaatcagtgaggcacctatctcagcgatctgtctatttcgttcatccatagttgcctgactccccgtcgtgtagataactacgatacgggagggcttaccatctggccccagtgctgcaatgataccgcgagacccacgctcaccggctccagatttatcagcaataaaccagccagccggaagggccgagcgcagaagtggtcctgcaactttatccgcctccatccagtctattaattgttgccgggaagctagagtaagtagttcgccagttaatagtttgcgcaacgttgttgccattgctacaggcatcgtggtgtcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtctaagaaaccattattatcatgacattaacctataaaaataggcgtatcacgaggccctttcgtcttcaagaa
taaagcaatagcatcacaaatttcacaaataaagcattTttcactgcattctagttgtggtttgtccaaactcatcaatgtatcttatcatgtct...5860

FIG. 3C

NS3 (HCV Serine Protease/Helicase)

NS5B (HCV RDRP)

HCV Core

Firefly Luciferase

*(C) = coding sequence of luciferase gene,
(A) = antisense sequence of luciferase gene,
(C/A) = single tube RT-PCR; does not differentiate between coding and non-coding strand.

IN VITRO SYSTEM FOR REPLICATION OF RNA-DEPENDENT RNA POLYMERASE (RDRP) VIRUSES

CROSS-REFERENCE TO RELATED APPLICATIONS

This application claims the benefit of U.S. Provisional Application No. 60/265,437, filed Jan. 31, 2001, the contents of which are herein incorporated by reference in their entirety.

FIELD OF THE INVENTION

This invention is directed toward the pharmaceutical and molecular biology arts, more particularly this invention is an in vitro system for the replication of the viral genomes of viruses that depend upon the enzyme RNA-dependent RNA polymerase (RDRP) for replication. The method of the invention provides an efficient means for measuring genomic replication in RDRP viruses, and also for the rapid screening of compounds for their ability to inhibit genomic replication of RDRP viruses, including the Hepatitis C virus (HCV).

BACKGROUND OF THE INVENTION

It is known that viral genomes can be made of DNA or RNA and can be double-stranded or single-stranded. Typically, viral genomes encode viral coat proteins that serve to package the genome after replication, and also nonstructural proteins that facilitate enzymatic replication of the viral genome in conjunction with cellular enzymes. In the case of some viruses having a single-stranded RNA genome, one of the nonstructural proteins encoded by the viral genome is RNA-dependent RNA polymerase (RDRP), which is needed by the virus to replicate its genomic sequence. The viral enzyme RNA-dependent RNA polymerase is also called RNA replicase.

The viral family Flaviviridae is one such type of virus which is dependent upon its own RNA-dependent RNA polymerase in order to replicate. Flaviviridae is a family of viruses having a single-stranded RNA genome in the (+) orientation. The term "(+) orientation" is a convention used to designate single-stranded nucleic acid molecules which exist in the coding or sense orientation when read from the 5' to 3' direction. The Flaviviridae family comprises the flaviviruses, the animal pathogenic pestiviruses, the recently characterized GB viruses (GBV-A, GBV-B and GBV-C/hepatitis G), and most importantly from a human disease perspective, the genus Hepacivirus or Hepatitis C virus (HCV). The RNA genome of these viruses typically includes a single long open reading frame encoding a polyprotein that is proteolyically cleaved into a set of distinct structural and nonstructural protein products. Translation of the open reading frame of the genome is directed via a 5' untranslated region (UTR) which functions as an internal ribosomal entry site (IRES). The 3' end of the genome in these viruses comprises a highly conserved UTR region of variable length which is thought to be essential for replication.

The most well-known member of the Flaviviridae family of viruses is the Hepatitis C virus ("HCV"), which is a parenterally transmitted, hepatotropic virus that in primates causes acute and chronic hepatitis, as well as hepatocellular carcinoma. Approximately 2% of the world's human population is thought to be afflicted with HCV infections. No vaccine for HCV is currently available, and present treatment is generally limited to interferon monotherapy, or the combination of alpha-interferon with the nucleoside analog ribavirin. (1)(2)(3)(4)(5).

HCV is a positive-stranded RNA virus having a genome 9.6 kb long comprised of a single, uninterrupted open reading frame encoding a polyprotein of about 3000–3011 amino acids. The HCV polyprotein is a precursor to the individual HCV proteins necessary for replication, packaging and infectivity. The structural region of the polyprotein precursor (including the C, E1, E2 and p7 proteins) is processed by host cell signal peptidases. The nonstructural region of the precursor (including the NS2, NS3, NS4A, NS4B, NS5A and NS5B proteins) is processed between NS2 and NS3 by NS2–3 protease, while processing in the NS3-NS5B region of the polyprotein is accomplished by NS3 protease activity. (6)(7)(8)(9)(10).

The mode of replication of the HCV virus is still speculative and current understanding is based upon analogy with other of the flavi-and pestiviruses. It is believed that HCV replication begins by viral penetration of the host cell and liberation of the viral genomic (+)single-stranded RNA from the virus particle into the cytoplasm of the cell. The viral RNA is translated by cellular enzymes, and the encoded viral polyprotein is processed into several distinct functional viral proteins including RNA-dependent RNA polymerase protein (RDRP). RDRP then proceeds to synthesize (–)stranded RNA intermediates (from template viral genomes) which in turn serve as templates for synthesis of new (+)stranded RNA molecules. These (+)stranded viral RNA molecules can then be used for further viral polyprotein expression, for synthesis of new (–)stranded RNA molecules, or for packaging into progeny virions which can then be released from the infected cell to spread the HCV infection. (1).

Presently, there are no efficient systems for in vitro monitoring of the replication of the RDRP viruses of the Flaviviridae family. As a result, there is a lack of means for studying the mechanism of replication of these (+) stranded RNA viruses, or for determining the ability of a compound or condition to inhibit such replication. While cell-based systems for HCV replication have been described (11), these systems rely on protocols and endpoints that are not easily formatted into platforms for screening large numbers of compounds for anti-viral activity (12). The present invention provides a solution to these problems by providing a system for the efficient in vitro manipulation and monitoring of the replication of RDRP viruses. The system of the invention can be assembled so as to provide a convenient platform for screening inhibitors to RDRP viral replication. The method of the invention also provides a means to design therapies for the in vivo treatment of cells that are infected with RDRP viruses.

SUMMARY OF THE INVENTION

The present invention provides an efficient in vitro method for measuring the replication of the genome of viruses that are dependent upon RNA-dependent RNA polymerase for replication (these types of viruses are herein referred to as "RDRP viruses"). The method comprises the steps of culturing virally-compatible eukaryotic cells, which have been transfected with the cDNA of the genome of the RDRP virus, and transfecting these cultured cells with a construct of the invention, which construct comprises the cDNA, in antisense orientation, of a reporter gene sequence. The reporter gene cDNA sequence of the construct is operably linked on its 5' end with the cDNA of the untranslated region (hereinafter "UTR") in antisense orientation of the native 3' end of said RDRP virus, and is operably linked on its 3' end with the cDNA of the UTR in antisense orientation of the native 5' end of said RDRP virus. Thus, the construct will be comprised of the cDNA, in antisense orientation, of a reporter gene flanked by the 3' and 5' UTRs of the native RDRP viral genome. Transfected cells containing the construct of the invention are cultured for a sufficient period of time under conditions which are permissive for replication of said RDRP virus, and the cells are analyzed for the presence of the protein encoded by the reporter gene. If the cDNA of the RDRP viral genome has been replicated and processed within the cultured cell, viral RDRP enzyme will have been synthesized, thereby enabling polymerization of the construct and synthesis of the protein encoded by the reporter gene. Thus, detection of the reporter protein in the cells provides a means to monitor and measure the genomic replication of said RDRP virus.

In another aspect, the invention provides an efficient in vitro method for identifying compounds or conditions which inhibit the genomic replication of viruses that are dependent for replication on RNA-dependent RNA polymerase (an RDRP virus). The method comprises the steps of culturing virally-compatible eukaryotic cells, which have been transfected with the cDNA of all or a portion of the genomic sequence of the RDRP virus, and transfecting these cultured cells with a construct of the invention, which comprises the cDNA in antisense orientation of a reporter gene sequence. The reporter gene cDNA sequence is operably linked on its 5' end with the cDNA of the untranslated region (UTR), in antisense orientation, from the native 3' end of said RDRP virus, and is operably linked on its 3' end with the UTR, in antisense orientation, from the native 5' end of the RDRP virus. The cultured cells are exposed to a compound or condition suspected of being capable of inhibiting the genomic replication of the RDRP virus, and thereafter or concurrently the cells are cultured for a period of time under conditions which are permissive for genomic replication of the RDRP virus. The cells are analyzed for the presence of the protein encoded by the reporter gene sequence, whereby a decrease in the level of the reporter protein indicates that the suspected compound or condition is capable of inhibiting genomic replication of the RDRP virus.

The present invention also provides a method of selectively affecting a cell which is infected with a virus that is dependent for genomic replication upon RNA-dependent RNA polymerase (an RDRP virus). The method comprises transfecting tissues, or cells which are infected with an RDRP virus, with a construct of the invention comprising the cDNA in antisense orientation of a gene or sequence which encodes a protein that is capable of affecting the cell, wherein the cDNA sequence encoding said protein is operably linked on its 5' end with the cDNA of the untranslated region (UTR), in antisense orientation, of the native 3' end of said RDRP virus and is operably linked on its 3' end with the cDNA of the UTR, in antisense orientation, of the native 5' end of said RDRP virus. Sufficient time for genomic replication of said RDRP virus is allowed. Thus, upon genomic replication of the RDRP virus, RNA-dependent RNA polymerase (RDRP) is produced which will cause polymerization of the construct thereby allowing synthesis within infected cells of the affecting protein. In this manner, only cells that are infected with the RDRP virus will be affected, thereby affording a mechanism to selectively affect RDRP virally infected cells within a mixed population of infected and normal cells. In a preferred aspect of this embodiment of the invention, the effect achieved is to selectively harm or kill cells which are infected with the RDRP virus by inserting into the construct the cDNA of a sequence encoding a protein which is harmful or fatal to the cell.

In all aspects of the present method of the invention, a preferred embodiment includes wherein the RDRP virus is selected from the viral family Flaviviridae. It is most preferred that the RDRP virus is HCV.

A further preferred embodiment in all aspects of the method of the invention includes wherein the construct of the invention further comprises the cDNA of a delta ribozyme sequence, in sense orientation, operably linked to the 3' end of the construct adjacent to the 3' end. When the RDRP virus is HCV, the cDNA of hepatitis delta ribozyme, in sense orientation, is operably linked to the 3' end of the cDNA of the 5' UTR of the native HCV viral genome.

In another aspect, the invention provides a construct comprising the cDNA, in antisense orientation, of a reporter gene sequence wherein said reporter gene cDNA sequence is operably linked on its 5' end with the cDNA of the UTR, in antisense orientation, of the native 3' end of an RDRP virus and is operably linked on its 3' end with the cDNA of the UTR, in antisense orientation, of the native 5' end of the RDRP virus. Alternatively, in another aspect of the invention, instead of the antisense cDNA of a reporter gene sequence, a construct may comprise the antisense cDNA of an "affecting gene" wherein said gene encodes a protein which is capable of affecting the cell, preferably harming or killing the cell. In these aspects of the invention it is preferred that the RDRP virus is HCV.

The constructs of the invention further comprise an operably linked constitutive or inducible promoter.

It is also preferred that the constructs of the invention further comprise the cDNA, in sense orientation, of the hepatitis delta ribozyme operably linked to the 3' end of the cDNA, in antisense orientation, of the 5' UTR of the native viral genome.

And in another aspect, the invention provides a eukaryotic cell which has been transfected with a construct of the invention, preferably a primate cell, most preferably, a human cell.

BRIEF DESCRIPTION OF THE DRAWINGS

FIG. 3. Nucleotide sequence of pMJ050, presented from left to right in 5' to 3' orientation, FIG. 3A. showing the nucleotides comprising the SV40 promoter and the HCV 3'UTR (in antisense orientation); FIG. 3B. showing the luciferase coding region (in antisense orientation); the HCV 5' UTR sequence (in antisense orientation); and the hepatitis delta virus ribozyme sequence (in sense orientation); and FIG. 3C. showing the plasmid backbone sequence.

DETAILED DESCRIPTION OF THE INVENTION

Figure 1:
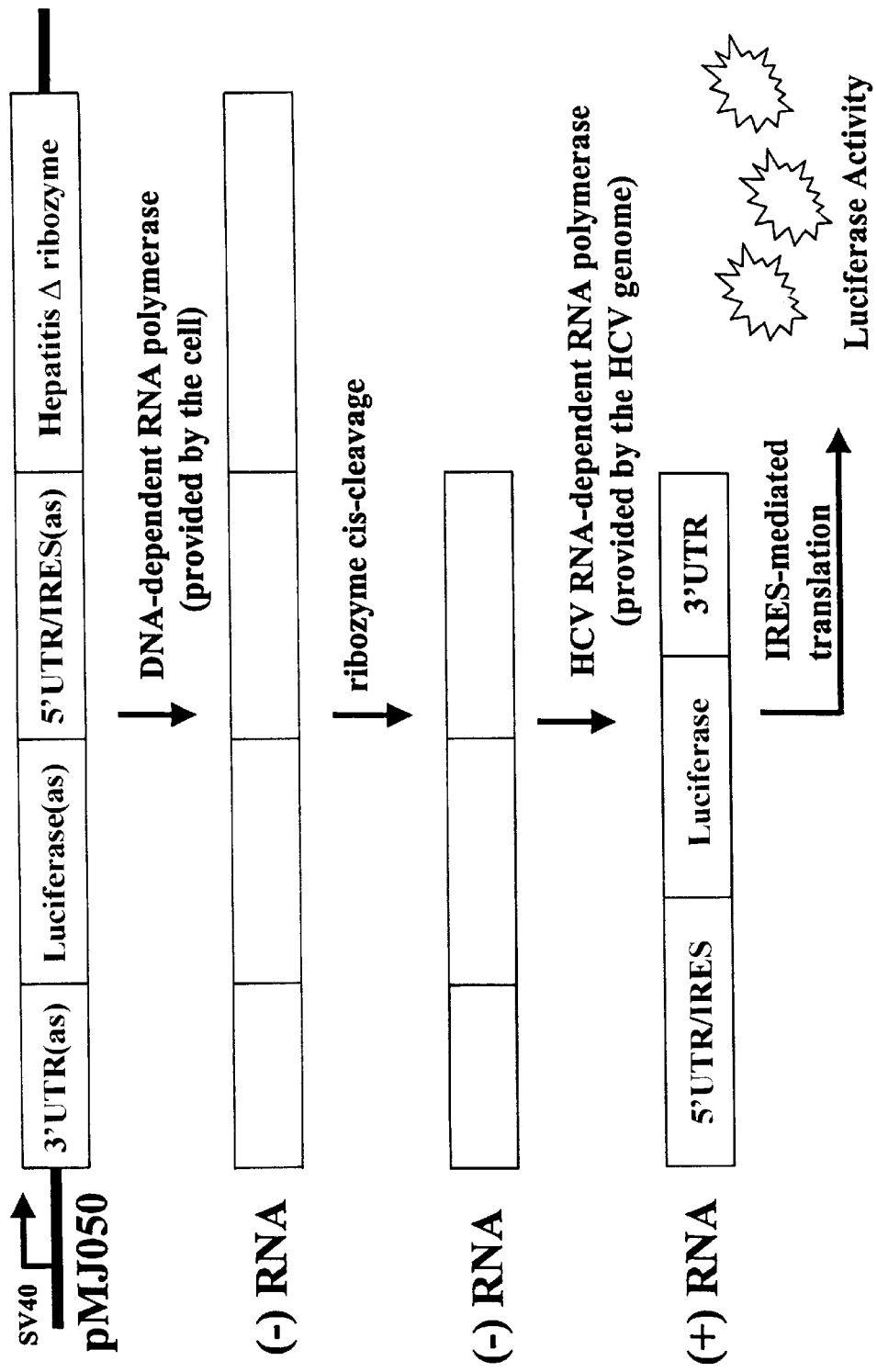
FIG. 1. Schematic for production of RDRP-dependent luciferase activity in the 293B4α cell line.

A convenient in vitro system that models viral replication for several members of the important viral family Flaviviridae has not been described to date. This lack of an in vitro system has significantly hindered research in this field directed towards development of antiviral agents for the treatment of viral infection, particularly for HCV infection. Described herein is an in vitro system that can be formatted to allow detection of cells in which RDRP genomic replication is occurring. The method employs a construct that expresses a detectable reporter protein in response to RDRP viral genomic replication. The method of the invention can be manipulated to screen for compounds or conditions having the ability to inhibit RDRP viral genomic replication. The method also provides a mechanism in which RDRP virally-infected cells can be selectively affected.

Various definitions and abbreviations are provided throughout this document. Most words, unless otherwise defined, have the meaning that would be attributed to those words by one skilled in the art of the invention.

The following abbreviations are used throughout this application: HCV: Hepatitis C virus; DNA: deoxyribonucleic acid; RNA: ribonucleic acid; UTR: untranslated region; hdvribo: hepatitis delta virus ribozyme; PCR: polymerase chain reaction; RDRP: RNA-dependent RNA polymerase enzyme; IRES: internal ribosome entry site; RT: reverse transcriptase; and RT-PCR: reverse transcription polymerase chain reaction.

As used herein the term "in vitro" means occurring outside of a living organism; in contrast to the term "in vivo", which means occurring within a living organism. In vitro can describe processes and conditions occurring within cultured cells, or occurring within cellular lysate systems that contain the cellular components necessary to perform the process in question.

Applicants contemplate that the in vitro methods of the invention relating to measuring RDRP genomic replication and identifying inhibitors of such replication can be conducted in cell culture systems, or alternatively, in the cellular lysate systems of virally compatible eukaryotic cells.

Within the context of this invention, the term "virally-compatible cells" refers to eukaryotic cells that contain the necessary cellular proteins required by the RDRP virus to complete replication of the virus genome. Virally-compatible cells include, but are not limited to, cells in which the viral particle is able to complete its entire replication cycle i.e., the virus is able to reproduce and generate other infectious viral particles. Also included are cells that may not be able to sustain the entire viral replication cycle, but which are able to sustain the replication of the viral RNA genome. Examples of preferred virally-compatible cells include mammalian, especially human, liver and kidney cells, and B and T cells.

"Virally-compatible cells which have been transfected with the cDNA of the genomic sequence of an RDRP virus" refers to virally-compatible cells into which have been stably incorporated a functional genomic sequence of the virus under study. When the method is conducted in order to study and measure replication of the viral genome, it will be preferable to incorporate most or all of the native viral genomic sequence, in order to most effectively mimic and study native replication. When the method is conducted in order to identify inhibitors of viral replication, it is possible to incorporate into the cellular genome all of the genome, or alternatively only those selective portions of the viral genome which encode proteins to be studied, so long as the selected portion of the viral genome includes the sequence that encodes the RNA-dependent RNA polymerase, which is known as the NS5B portion of the HCV genome. Methods for stably transfecting all or selective portions of he viral genome into suitable cell lines are known by those skilled in the art. For example, such methods are reported in "Continuous Human Cell Lines Inducibly Expressing Hepatitis C Virus Structural and Nonstructural Proteins," Darius Marpour, Petra Kary, Charles M. Rice and Huber E. Blum (1998) *Hepatology* 28:192201. "Transfection of a Differentiated Human Hepatoma Cell Line (Huh7) with In Vitro-Transcribed Hepatitis C Virus (HCV) RNA and Establishment of a Long-Term Culture Persistently Infected with HCV," Young J. Yoo et al, J. of Virology, Vol 69, No.1, Jan 1995, p. 32–38. Genomic sequences for the flaviviruses are generally available in the scientific literature, for example, see the Genbank library of sequences, in which includes viral and the flavivirus gene sequences.

Applicants contemplate that the in vitro methods of the invention relating to measuring genomic replication of RDRP cells and identifying inhibitors of such replication can be conducted not only in cell culture systems of virally-compatible cells, but also in cell lysate systems of those cells. For example, cells from HCV-infected cell culture or tissues removed from an HCV-positive individual can be used to create a cell lysate that can serve as a source of the HCV replicative proteins. This lysate can be prepared by lysing the infected culture or tissue cells by methods well known in these art, for example, by chemical or physical means, and clarifying the cell lysate of macromolecule cellular debris by centrifugation. Reporter RNA produced by in vitro transcription of the reporter constructs of the invention can be added to the cell lysate described above and the lysate with added reporter RNA can be incubated under proper conditions permissive for genomic replication. Such conditions (e.g., temperature, pH, salt concentrations, etc.) are known or can be readily determined experimentally by those skilled in the art for the particular system selected for the assay. Lysates are then assayed to see if the reporter protein has been produced, thereby indicating that viral genomic replication has occurred within the lysate system. Such lysate systems are amenable to rapid, high throughput screening for inhibitors of RDRP viral replication.

The term "replication" as used within the disclosure herein regarding viruses relates to the replication of the genome of the virus, rather than whole virus replication which results in an infectious particle.

The term "transfecting" as used herein refers to the process of inserting heterologous DNA into a eukaryotic cell by chemical, physical or other means that include but are not limited to liposomal transfer, in which liposomal micelles containing the heterologous DNA transfer the DNA into the cell by fusion with the cell membrane; $CaPO_4$ or DEAE-dextran shock, in which these chemical moieties physically disrupt the cell membrane allowing macromolecules to pass from the outside to the inside of the cell; and electroporation, in which electrical shock is used to disrupt the cell membrane allowing macromolecules to pass from the outside to the inside of the cell. Such methods are well known in these arts. Newly emerging nucleic acid delivery systems include the adenoviral and adeno-associated viral systems, which are being developed and used to deliver heterologous DNA sequences into human tissues for the purposes of gene therapy. Also, as used herein, the term "transfected" includes both stably transfected cells, in which the transfected DNA recombines with the host cell DNA such that it becomes a permanent part of the genome of the host cell, and also transiently transfected cells, in which the transfected DNA remains independent of the host cell DNA and is either destroyed by host cell mechanisms which act to defend the cell from "infection" with heterologous DNA or is diluted out by the replication of the host cell.

Moreover, the RNA which is used as the template for replication can be delivered to the cell by methods including but not limited to virus infection, transfection of in vitro transcribed RNA, and transcription of DNA that is stably or transiently transfected into the host cell. RNA transcription from stably or transiently transfected heterologous DNA can occur either constitutively or inducibly.

Within the context of the invention, those skilled in this art will understand that transcription of transfected DNA will be driven by an operably linked promoter system. A "promoter" is a regulatory nucleic acid sequence that is capable of controlling the expression of a coding sequence or functional RNA. In general, a coding sequence will be located 3' to the promoter sequence. Promoters may be derived in their entirety from a native gene, or be comprised of different elements derived from different promoters found in nature. It is understood that various well known promoters are suitable to direct expression of any number of different coding sequences depending on cell and tissue type, in response to different stimuli, or at different stages of cellular or tissue development. Furthermore, the promoter sequence, which is part of the transfected DNA of the invention, will determine if expression of the transfected DNA will be constitutive or inducible. Examples of constitutive promoters include but are not limited to the cytomegalovirus immediate-early promoter, the SV40 viral promoter, human immunodeficiency virus long terminal repeat promoter, and the chicken beta-actin promoter. Examples of inducible promoters include but are not limited to the tetracycline-responsive promoter, the ecdysone-inducible promoter, and the mifepristone-inducible promoter.

The term "operably linked" refers to the association of two or more nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences such as promoters in the sense or antisense orientation.

The term "RNA-dependent RNA polymerase virus" or "RDRP virus" means a virus which is dependent upon a functional RNA-dependent RNA polymerase for the replication of its nucleic acid genome and the production of infectious virus. In particular relating to the present invention, we include viruses that are members of the Flaviviridae family. It has been shown that the replication of all of the members of this virus family are dependent upon the virus's RNA-dependent RNA polymerase for replication of the virus genome. The RDRP performs several essential steps in the replication of RNA including the interaction of the RDRP with the 3' and 5' untranslated regions (UTR) of the genome, initiation of the synthesis of the new RNA strand, and continued elongation of the growing progeny RNA. The UTR's for each of the different members of this family are unique to that particular virus, and have been identified, sequenced and placed in the public domain (i.e., Genebank data base), and are thus readily obtainable. In a preferred aspect of this invention the sequence for the ribozyme from the hepatitis delta virus is placed at the 3' end of the constructs of the invention. This sequence, when transcribed into RNA, has catalytic function and will cleave itself from the 3' end of the RNA transcript. When using HCV, for example, this cleavage event results in a proper 3' end for the HCV 3' UTR in the antisense RNA transcripts and a proper 5' end in the HCV 5' UTR in the sense RNA transcripts of this invention. The catalysis of the hepatitis delta virus ribozyme is regulated by sequences contained within the ribozyme itself. This being so, the sequence for the hepatitis delta ribozyme included in the description of this construct can be used with other RDRP virus systems (besides HCV) and accordingly in most or all of the antisense reporter constructs of the invention.

Within the context of the present invention, the term "expression" refers to the transcription of DNA resulting in the production of sense or antisense RNA, and may also refer to translation of mRNA into a polypeptide, such as the reporter protein.

The term "reporter gene" or "reporter gene sequence" refers to any gene encoding a protein which can be expressed and conveniently detected in a eukaryotic cell including chemically, spectrophotometrically, immunologically, calorimetrically, radioactively or through a receptor-mediated cascade system. Examples of reporters include but are not limited to luciferase, secreted alkaline phosphatase, beta-galactosidase, hepatitis B virus surface antigen, herpes simplex virus thymidine kinase, genticin-resistance, zeocin-resistance, hygromycin-resistance, and puromycin-resistance.

A reporter gene sequence affects cells or lysates within the method of the invention by producing an effect that can be detected. Applicants contemplate that other gene sequences could be used in place of a reporter sequence when the goal of the researcher is to selectively produce another specific effect within cells wherein viral genomic replication is occurring. Thus, if a gene or genes resulting in a deleterious effect are selected for insertion into the construct in place of (or in addition to) the reporter sequence, the method of the invention offers a mechanism to design therapeutic methods for the selective treatment of cells infected with a flavivirus, wherein the construct containing an affecting gene or genes is delivered in vivo to cells known to be infected with a replicating flavivirus.

The term "construct" when referring to the "construct of the invention" as used herein refers to a DNA sequence which comprises a coding sequence for a reporter gene or an affecting gene, as the terms are used herein, plus regulatory sequences related to expression of that coding sequence including particularly promoters that facilitate transcription of the coding sequence and also including any 5' and/or 3' transcribed but untranslated sequences that are associated with the coding sequence and may be required, plus the 3' and 5' untranslated regions (UTRs) of the RDRP virus under study. These sequences may be in the sense or antisense orientation. The total construct sequence is created using standard molecular biology techniques. The construct of the invention may also include an operably linked ribozyme sequence.

A representative construct of the invention is provided in FIG. 1, and includes (from 5' to 3') an SV40 promoter sequence, in sense orientation, operably linked to the HCV 3'UTR, in antisense orientation, linked to a coding sequence for luciferase protein, in antisense orientation, linked to the HCV 5'UTR, in antisense orientation, linked to the coding sequence for the hepatitis delta ribozyme, in sense orientation, wherein said construct is delivered to the cell via the plasmid entitled pMJ050.

In one aspect of the invention, a method is provided for screening inhibitors of viral replication. Compounds and conditions that are potentially capable of inhibiting viral replication include but are not limited to small molecular weight synthetic chemicals, organic compounds that are derived from living or once living organisms, synthetic chemical compounds based on organic compounds derived from living or once living organisms, as well as various conditions including different frequencies of sound, and various wavelengths of light and temperature. By example, compounds may include small molecules, peptides, proteins, sugars, nucleotides or nucleic acids, and may be natural or synthetic.

The method of screening compounds for inhibitors of viral replication includes any protocol which utilizes cells or cell lysate containing all or a portion of a viral genome sufficient to express a functional RNA-dependent RNA polymerase, to which cell or lysate, is added the appropriate reporter construct of the invention. The viral genome and reporter construct system are placed in the presence of a potential inhibitor(s) of viral replication, under conditions amenable to replication of that viral genome. Thus, compounds or conditions capable of inhibiting replication of the viral genome, and/or capable of inhibiting the functionality of the expressed RDRP enzyme, can be identified via inhibition of expression of the reporter sequence.

The methods of the invention are functional when enough of the viral genome is present in the system to result in production of functional RNA-dependent RNA polymerase. Thus, the coding sequence of the viral genome that is used in the cultured cells or cell lysate can contain the coding sequence of the RNA-dependent RNA polymerase as part of the entire viral genome, or alternatively, it can contain subgenomic fragments of the viral genome, encoding, for example in HCV, the NS2 to NS5b region, or from the NS3 to NS5b region. In light of this aspect, the methods of the invention permit screening for inhibitors which have the ability to inhibit not only the NS5b RDRP, but also the NS2 protease, NS3 protease, and NS3 helicase as well, individually or collectively. Specifically, the ability to screen compounds for the potential to inhibit many different targets allows for the testing of different combinations of inhibitors targeted at one or more of the essential enzyme functions establishing whether interaction between the compounds favorably or deleteriously effects the ability of the compounds to inhibit the replication of the RNA.

EXAMPLES

The following examples demonstrate the method of the invention, but should not be viewed as limiting of the scope of the invention. Based upon the present disclosure many possible variations of the method of the invention will become apparent to those skilled in these arts.

In Examples 1 through 3 examines HCV viral genomic replication in human kidney cells, using firefly luciferase as a reporter gene within the construct of the invention. Example 3 demonstrates use of the method to confirm known inhibitors of HCV replication using the method of the invention. Example 4 demonstrates a semi high-throughput screening assay for inhibitors or HCV genomic replication.

Example 1

It is known that Flaviviridae viral replication takes place through a step catalyzed by the viral RNA-dependent RNA polymerase (RDRP), an enzyme not normally found in eukaryotic cells. A substrate for HCV RDRP was selected that consists of an antisense sequence of the firefly luciferase gene, a common reporter gene used in cell biology. To make this sequence appear "HCV-like" it was flanked with the 5' and 3' untranslated regions (UTR) of the native HCV viral genome in the same orientation as they are found in the (−)strand of the HCV replicative intermediates. Using the convention employed herein, the orientation existing in the (−)strand of the RNA genome will be referred to as the antisense orientation when read from the 5' to 3' direction. To demonstrate a preferred embodiment of the method, the hepatitis delta ribozyme hdvribo was attached to the 3' end of the HCV 5' UTR sequence, such that when the hdvribo processes the RNA, the sequence integrity of the 5' UTR would be maintained (the strategy for the reporter is shown in FIG. 1). This was done because it is known to those skilled in the art that the 5' UTR also acts as an internal ribosomal entry site (IRES) (13), and it was desirable to keep the 5' UTR sequence as true as possible to that found in the native virus.

This construct was stably transfected into a 293 cell line (human embryonic kidney cells) and designated 293 FL#9 (this cell line had been previously transfected to contain a full length cDNA copy of the native HCV genotype 1b genome). The cell line containing the construct of the invention, 293B4α, was demonstrated to produce active, detectable luciferase as a result of genomic replication of the HCV viral genome.

Figure 2:
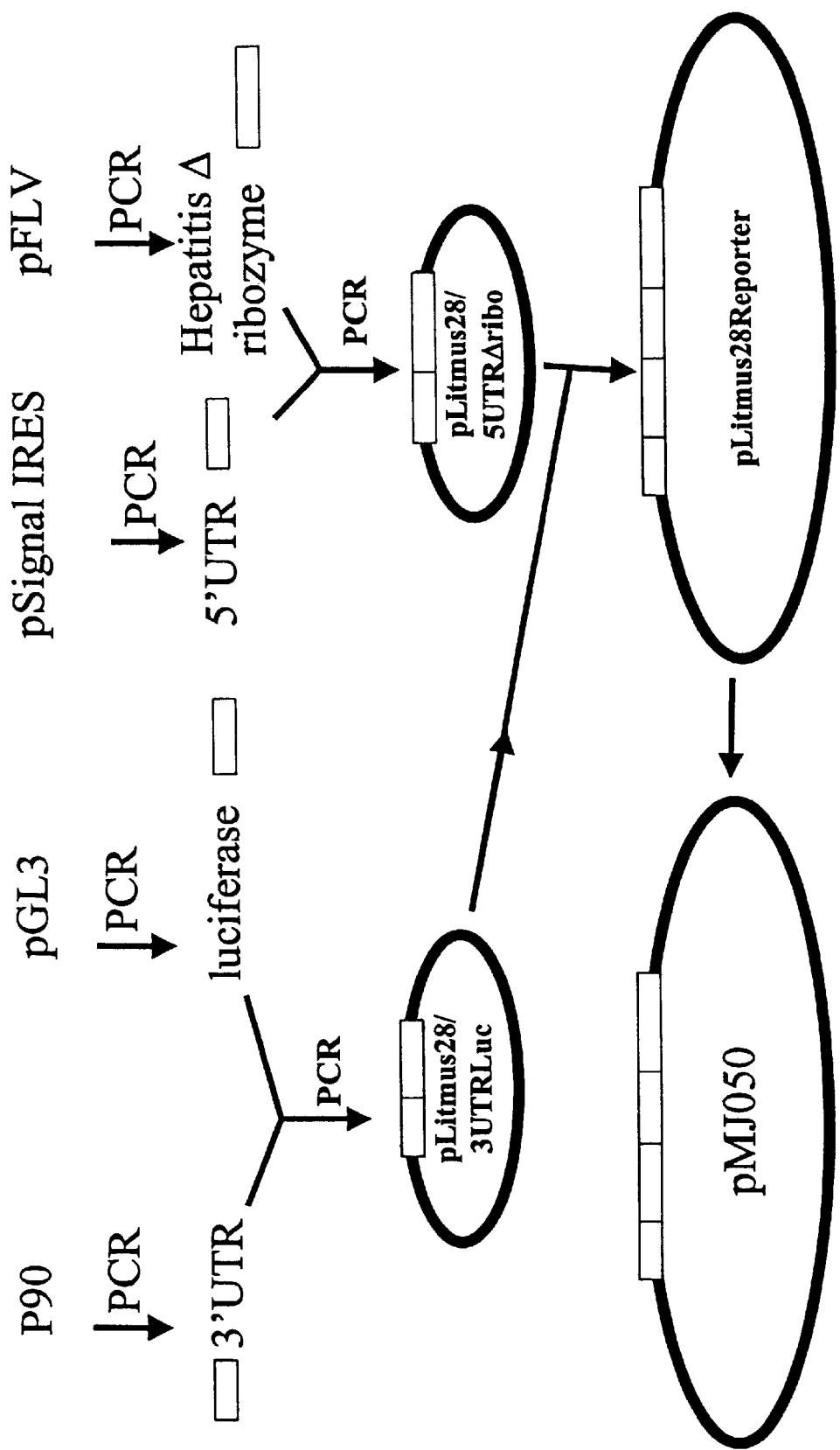
FIG. 2. Cloning strategy for the construction of pMJ050.

Preparation of the pMJ050 Construct pMJ050 was prepared in three steps. First, the antisense sequences of the 3' untranslated region of the HCV genome (3'UTR) and the firefly luciferase gene were joined together; second, the antisense sequence of the HCV 5' untranslated region (5'UTR) and the sense sequence of the hdvribo were joined together; and finally these two constructs were joined together resulting in a sequence which consisted of the antisense sequences of the "3'UTR-firefly luciferase-5'UTR-hdvribo (in the sense orientation)", respectively as read from 5' to 3' (FIG. 2).

Construction of the 3'UTR and luciferase sequence The antisense sequence of the HCV 3'UTR was PCR amplified from plasmid p90 (supplied by Dr. Charles Rice, Washington University at St. Louis) using PCR primers, 3'UTR5' (new) and 3'UTRHO (for the nucleotide sequences of all oligos, see Table 1). The antisense sequence of the firefly luciferase gene was PCR amplified from plasmid pGL3 (Promega Corporation, Madison Wis.) using PCR primers LUCHO and LUCIF3'. To join these two PCR products together, overlapping PCR was performed in which equimolar amounts of the two PCR products were mixed with oligos, 3'UTR5' and LUCIF3', and the DNA amplified by PCR.

TABLE 1

Nucleotide Sequences of Oligos Used to Create and Sequence pMJ050

| OLIGO NAME/<br>SEQ ID Nos: | OLIGO SEQUENCE (Read 5' TO 3') |
|---|---|
| 3'UTR5'new<br>SEQ ID NO:1 | GCG TTT AAG CTT ACA TGA TCT GCA GAG<br>AGG |
| 3'UTRHO<br>SEQ ID NO:2 | GGC GGA AAG ATC GCC GTG TAA AGG TTG<br>GGG TAA ACA CTC CGG |
| 5'UTR5'<br>SEQ ID NO:3 | CTG TGG ACG TCG GTT GGT GTT ACG TTT<br>GGT TTT TCT TTG AGG TTT AGG |
| 5'UTRHO<br>SEQ ID NO:4 | GGC TGG GAC CAT GCC GGC CGC CAG CCC<br>CCT GAT GGG GGC |
| LUCHO<br>SEQ ID NO:5 | CCG GAG TGT TTA CCC CAA CCT TTA CAC<br>GGC GAT CTT TCC GCC |
| LUCIF3'<br>SEQ ID NO:6 | TTG GTA GAC GTC CAA TGG AAG ACG CCA<br>AAA TAA AGA AAG G |

TABLE 1-continued

Nucleotide Sequences of Oligos Used to Create and Sequence pMJ050

| OLIGO NAME/ SEQ ID Nos: | OLIGO SEQUENCE (Read 5' TO 3') |
|---|---|
| HEPHO SEQ ID NO:7 | GCC CCC ATC AGG GGG CTG GCG GCC GGC ATG GTC CCA GCC |
| RIBOHD3' SEQ ID NO:8 | CTC AAG CTC TAG AGA GAT TTG TGG GTC CC |
| LUCACA (+) SEQ ID NO:9 | GAA GAC GCC AAA AAC ATA AAG AAG GGC CCG GCG CCA |
| LUCACA (−) SEQ ID NO:10 | TGG CGC CGG GCC CTT CTT TAT GTT TTT GGC GTC TTC |
| UTRRNA (+) SEQ ID NO:11 | CCT CTT AGG CCA TTT CCT GTT TTT TTT TTT |
| UTRRNA (−) SEQ ID NO:12 | AAA AAA AAA AAC AGG AAA TGG CCT AAG AGG |
| LUCFOR SEQ ID NO:13 | CCG AGT GTA GTA AAC ATT CC |
| LUCREV SEQ ID NO:14 | CTC GCA TGC CAG AGA TCC |
| LITFOR SEQ ID NO:15 | GAT CTT CGA ATG CAT CGC GCG C |
| LITREV SEQ ID NO:16 | GGC CTT GAC TAG AGG GTA CC |

The product of the overlapping PCR was digested with the restriction enzymes, Hind III and Aat II, and ligated into pLitmus28 (New England Biolabs, Beverley, Mass.) which had been linearized with Hind III and Aat II. The plasmid from the ligation reaction, pLitmus283'UTR luciferase was transformed into chemically competent E. coli DH5α cells. E. coli that had become transformed with this plasmid were selected by the ability to grow on solid nutrient agar containing ampicillin. Plasmid DNA was isolated from ampicillin-resistant bacterial cells and the sequence was verified by restriction enzyme analysis using BsrG I, Hind III and Aat II, and sequence analysis using sequencing oligos LUCFOR, LUCREV, LITFOR, and LITREV.

Construction of the Antisense 5'UTR and Sense Hdvribo Sequence

The sequence of the hepatitis delta virus ribozyme (hdvribo) was PCR amplified from plasmid pFullLengthVec (provided by Dr. William Mason, Fox Chase Cancer Center, Philadelphia, Pa. ) using PCR primers HEPHO and RIBOHD3'. The 5'UTR of the HCV genome was PCR amplified from plasmid pSignal IRES (provided by Robert Kovelman, Signal Pharmaceuticals, San Diego, Calif.) and joined to the hdvribo sequence by overlapping PCR using PCR primers 5'UTR 5', 5'UTRHO, and RIBOHD3'.

The DNA product from the overlapping PCR was digested with the restriction enzymes, Xba I and Aat II, and ligated into pLitmus28 that had been linearized by digestion with Xba I and Aat II. The recombinant plasmid, pLitmus285'UTRΔribo was transformed into chemically competent E. coli DH5 α cells. E. coli that had been transformed with this plasmid were selected by the ability to grow on solid nutrient agar containing ampicillin. Plasmid DNA was isolated from ampicillin-resistant bacterial cells and the sequence was verified by restriction enzyme analysis with Xba I and Aat II, and sequence analysis using primers 5'UTR5' and RIBOHD3'.

Construction of pMJ050

The inserts in plasmids, pLitmus283'UTR luciferase and pLitmus285'UTR hdvribo were joined together by digesting both plasmids with restriction enzymes Hind III and Aat II. Equimolar amounts of DNA were mixed and ligated together. The DNA resulting from the ligation reaction was transformed into chemically competent E. coli DH5α cells. E. coli that had become transformed were selected by the ability to grow on solid nutrient agar containing ampicillin. Plasmid DNA was isolated from ampicillin-resistant bacterial cells. Insertion of the reporter gene was verified by restriction enzyme analysis using Hind III and Xba I.

For the reporter gene to be transcribed in an eukaryotic cell, the reporter gene from pLitmus28reporter had to be placed into a plasmid that contained an eukaryotic promoter. To accomplish this, the reporter gene was removed from pLitmus28reporter by restriction digestion with Spe I and Xba I and ligated into the plasmid pZeoSV that had been previously linearized by restriction digest with Hind III and Spe I. The DNA resulting from the ligation reaction was transformed into chemically competent E. coli DH5α. E. coli that had become transformed were selected by the ability to grow on solid nutrient agar containing zeocin. Plasmid DNA was isolated from zeocin-resistant bacterial cells and the sequence of the recombinant plasmid was verified by restriction enzyme analysis using Hind III, TthIII I and Kpn I, and sequence analysis with oligos 3'UTR5' new, 3'UTRHO, 5'UTR 5', 5'UTRHO, LUCHO, LUCIF3', HEPHO, RIBOHD3', LUCFOR, and LUCREV. The plasmid containing the correct sequence construct was designated pMJ050 (FIG. 3).

Example 2

Creation of the 293B4α Cell Line (a) Transfection and Selection of Zeocin-Resistant 293FL#9 Cells.

To create a cell line the would express the antisense luciferase construct as RNA in the environment of the HCV proteins, pMJ050 was transfected into 293FL#9 cells by electroporation (3–10 μg of plasmid into $5 \times 10^6$ cells; one pulse at 960° F. and 0.2 kV in a BioRad electroporator). Transfectants were grown in the presence of 250 μg/ml each of G418 and zeocin for several weeks to select for cells that had stably integrated pMJ050 into their genome. Forty-eight zeocin-resistant stable transfectants were randomly selected and expanded further.

(b) Luciferase Assay

The 48 stable transfectants were tested for the ability to express active luciferase using the commercially available Luciferase Assay System (Promega Corp., Madison, Wis.) as directed by the manufacturer. Briefly, the $1 \times 10^6$ cells from each of the 48 clonal cell lines was lysed with 100 μl of Lysis Buffer. The lysates were clarified by centrifugation and stored at −80° C. Twenty microliters of cell lysate was assayed for luciferase activity by the addition of 100 μl of luciferin substrate and quantification on a luminometer.

Figure 4:
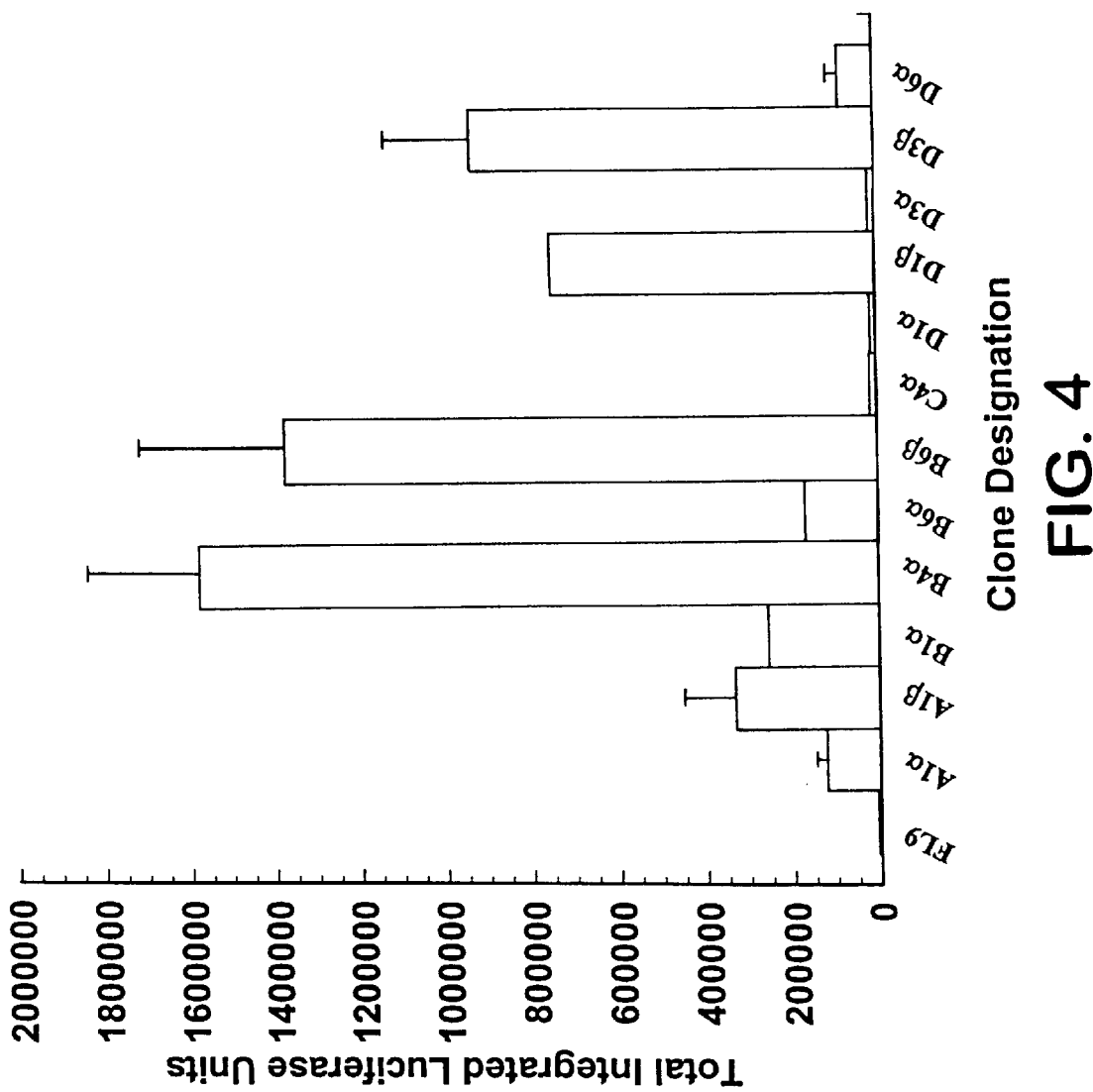
FIG. 4. Production of luciferase in 293FL#9 cells stably transfected with pMJ050.
Figure 5A:
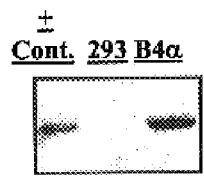
FIG. 5. Production of luciferase, HCV core, HCV serine protease, and HCV RDRP in the 293B4α cell line.
Figure 5B:
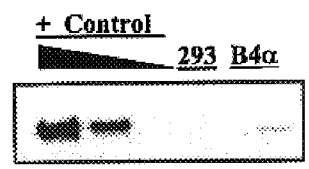
Figure 5C:
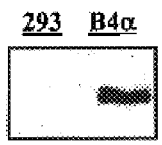
Figure 5D:
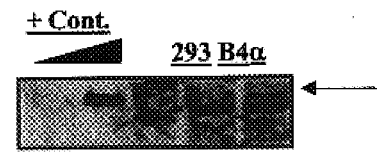

Twelve of 48 resultant clones expressed various amounts of luciferase activity. These twelve were grown for several more weeks in the presence of zeocin and G418 and then retested for luciferase activity (FIG. 4). The cell line, 293B4α consistently and reproducibly had the highest level of luciferase activity and was chosen for further study.

Characterization of the 293B4α Cell Line (a) Protein Production

Western blot analysis was used to determine if the 293B4α cell line was producing luciferase, HCV core, HCV serine protease (encoded by the HCV NS3 gene), and HCV RDRP (encoded by the HCV NS5b). Western blot analysis showed that all 4 proteins were produced in the 293B4α cell line (FIG. 5).

(b) Luciferase RNA Production

Theoretically, the only way for luciferase protein to be produced in 293B4α cells is if there is an RDRP present in the cells to transcribe the antisense luciferase RNA into the sense orientation. RT-PCR was used to determine (1) if antisense luciferase RNA transcription, driven by the SV40 promoter, was taking place, and (2) if the antisense RNA was being transcribed into sense luciferase RNA. Oligos LUCFOR and LUCREV were used in the RT-PCR to determine both of these.

Total cytoplasmic RNA was isolated from $5 \times 10^6$ 293B4α cells using the RNAgents RNA Isolation kit as directed by the manufacturers (Promega Corp., Madison, Wis.). An aliquot, which was equivalent to 1/50 of the RNA isolated, was used in each RT-PCR. To determine the presence of the antisense and sense strands of RNA, the RT portion of the reaction was run in the presence of only one of the oligos (i.e. LUCREV to detect the antisense strand and LUCFOR to detect the sense strand). The temperature of the reaction was increased to 95° C. for 5 minutes to heat inactivate the RT enzyme and then the other oligo was added and PCR proceeded as normal.

Figure 6:
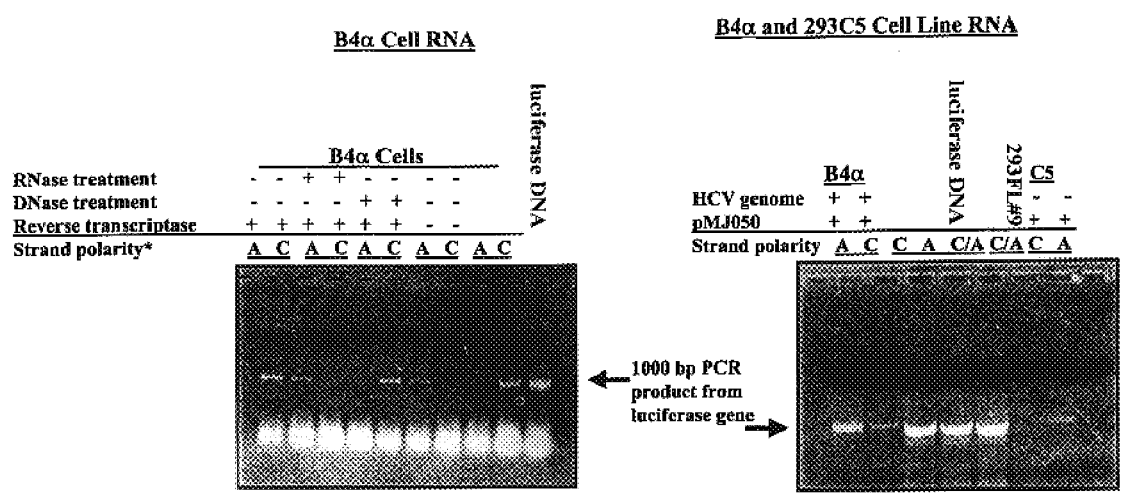
FIG. 6. Production of luciferase sense and antisense RNA in the 293B4α cell line.

The cytoplasm of the 293B4α cells contained both species of luciferase RNA, whereas 293FL#9 cells did not contain either species (FIG. 6). Likewise, if the RT step was eliminated from the RT-PCR or if the RNA samples were treated with RNase prior to the RT-PCR, no products were produced indicating that the product detected in the RT-PCR of the RNA of 293B4α cells was from RNA and not DNA contamination. Moreover, treating the RNA samples with DNase prior to RT-PCR had no effect on the quantity of product produced in the RT-PCR.

Example 3

Inhibition of Luciferase Activity by Inhibitors of Luciferase, HCV Serine Protease and IRES-Mediated Translation Four chemical compounds, two known to inhibit the HCV serine protease, one known to inhibit IRES-mediated translation of the HCV RNA, and one known to inhibit firefly luciferase in the 293B4α cell line, were tested for the ability to reduce the level of firefly luciferase in the 293B4α cell line. Thirty-five millimeter plates were seeded with $5 \times 10^5$ cells/plate and incubated at 37° C. overnight. Media containing various concentrations of the four chemical compounds were added to the cells. Forty-eight hours after the addition of compound, the cells were lysed with lysis buffer as described above. Luciferase activity was quantified using the Luciferase Assay System (Promega Corp., Madison, Wis.) as directed by the manufacturer. All four compounds had the ability to inhibit luciferase activity (Table 2).

TABLE 2

Inhibition of luciferase activity in the 293B4α cell line

| Compound | Inhibitor Class | Inhibition[1] |
|---|---|---|
| Cmpd A | HCV Protease | ++ |
| Cmpd B | HCV Protease | ++ |
| Cmpd C | HCV RDRP | + |
| Cmpd D | Luciferase | +++ |
| Vehicle (0.3% DMSO) | N/A | -- |

[1]Key to activity:
+++greater than 75% inhibition;
++between 75% and 50% inhibition;
+between 49% and 25% inhibition; and
--less than 25% inhibition.

Example 4

Semi High-Throughput Assay for Inhibitors of HCV Replication Using the 293B4α Cell Line The assay begins by plating 3000 293B4α cells/well in 96-well plates and incubating the cells at 37° C. overnight to allow for attachment of the cells to the bottom of the well. Sixteen to twenty-four hours after plating the cells, various concentrations of compound are added to the wells. Thirty-six to forty-eight hours after the addition of compound, media are removed from the cells and the cells are washed once with cold PBS. The cells are lysed in 25 µl of lysis buffer and the plates are stored at −80° C. The lysates are thawed at room temperature and 20 µl of lysate and 100 µl of luciferin substrate are placed into the well of an opaque microtiter plate. Luciferase activity is quantified with a luminometer. The potency of the individual compounds is calculated by linear regression. 293FL#9 cells were electroporated with pMJ050 and were selected in G418 and zeocin. Forty-eight clones were randomly selected and tested for the ability to produce luciferase. The luciferase activity in the twelve clones that were able to produce luciferase, was quantified and is shown in FIG. 4. The 293B4α cell line was selected for further study.

293B4α cells were lysed in lysis buffer and the proteins in the lysates were separated by size on a 4–12% polyacrylamide gel. The proteins were transferred to nitrocellulose by electrophoresis. Luciferase, HCV core, HCV serine protease, and HCV RDRP were detected by antibodies specific for the individual proteins.

Total cytoplasmic RNA was isolated for 293B4α cells using the RNAgents RNA Isolation kit as directed by the manufacturer (Promega Corp., Madison, Wis.). RT-PCR and 2% of each RNA sample was used to produce DNA from either the sense or antisense luciferase RNA. C=sense orientation of the luciferase gene (coding); A=antisense orientation of the luciferase gene (non-coding); and A/C=single tube RT-PCR, does not differentiate between the coding and non-coding species of RNA. Plasmid DNA containing the luciferase gene was used as a positive control for the RT-PCR. (FIG. 6)

All references cited within this disclosure are hereby incorporated by reference in their entirety.

REFERENCES

1. Bartenschlager and Lohman (2000) J. Gen. Virol. 81, 1631–1648.
2. Kolykhalov et al. (1997) Science 277, 570–574.
3. Neuman et al. (1998) Science, 282, 103–107.
4. Tong et al. (1995) Lancet 345, 1058–1059.
5. Saito et al. (1990) Proc. Natl. Acad. Sci. USA 87, 6547–6549.
6. Bartenschlager et al. (1994) J. Virol. 68, 5045–5055.
7. Eckart et al. (1993) BBRC 192, 399–406.
8. Grakoui et al. (1993) J. Virol. 67, 2832–2843.
9. Lin et al. (1994a) J. Virol. 68, 5063–5073.
10. Lin et al. (1994b) J. Virol. 68, 8147–8157.
11. Lohmann V., Korner F., Koch J. O., Herian U., Theilmann L. and Bartenschlager R. (1999) Replication of subgenomic hepatitis C virus RNAs in a hepatoma cell line. Science. 285:110–113.
12. Ohishi M., Sakisaka S., Harada H., Koga H., Taniguchi E., Kawaguchi T., Sasatomi K., Sata M., Kurohiji T. and Tanikawa K. (1999) Detection of hepatitis-C virus and hepatitis-C virus replication in hepatocellular carcinoma by in situ hybridization. Scandinavian J. Gastroenterology. 34:432–438.
13. Rijnbrand R. C. A. and Lemon S. M. (2000) Internal ribosomal entry site-mediated translation in hepatitis C virus replication. In, Current Topics in Microbiology and Immunology, Eds. Hagedorn, C. H. and Rice, C. M. pp. 85–116. Springer-Verlag Berlin.

What is claimed is:

1. An in vitro method for measuring the replication of a genomic sequence of a virus that is dependent for replication upon RNA-dependent RNA polymerase (an RDRP virus) comprising the steps of:
   a) culturing virally-compatible eukaryotic cells which have been transfected with the cDNA of the genomic sequence of said RDRP virus;
   b) transfecting said cultured cells with a construct comprising a cDNA, in antisense orientation, of a reporter gene sequence wherein said reporter gene cDNA sequence is operably linked on its 5' end with cDNA of the untranslated region (UTR) comprising an HCV IRES element and a HCV replication element, in antisense orientation, of the native 3' end of said RDRP virus and is operably linked on its 3' end with the cDNA of the UTR, in antisense orientation, of the native 5' end of said RDRP virus wherein the construct further comprises the cDNA, in the sense orientation, of a delta ribozyme operably linked to the 3' end of the 5'UTR sequence;
   c) culturing said cells for a sufficient period of time under conditions which are permissive for replication of said RDRP virus; and
   d) analyzing the cells for the presence of the protein encoded by the reporter gene sequence,
whereby detection of said protein provides a means to measure the genomic replication of said RDRP virus.

2. The method of claim 1, wherein the RDRP virus is a member of the Flaviviridae family.

3. The method of claim 2, wherein the RDRP virus is HCV.

4. The method of claim 1, wherein virally-compatible eukaryotic cell is a human cell.

5. The method of claim 4, wherein the virally-compatible eukaryotic cell is a human liver or kidney cell.

6. The method of claim 3, wherein the virally-compatible eukaryotic cells of step (a) are from the human cell line 293 FL#9.

7. The method of claim 1 wherein at step (b), transfection of cultured cells is performed using the method selected from: electroporation, liposomal transfer, CaPO$_4$ shock, and DEAE-dextran shock.

8. The method of claim 1, wherein the reporter gene is selected from: luciferase, secreted alkaline phosphatase, beta-galactosidase, Hepatitis B virus surface antigen, herpes simplex virus thymidine kinase, genticin-resistance, zeocin-resistance, hygromycin-resistance, and puromycin-resistance.

9. The method of claim 8, wherein the reporter gene is luciferase.

10. The method of claim 1 wherein the construct at step (b) comprises SEQ ID NO: 18.

11. The method of claim 1 wherein the construct at step (b) comprises SEQ ID NO: 18.

* * * * *

SEQUENCE LISTING

<160> NUMBER OF SEQ ID NOS: 20

<210> SEQ ID NO 1
<211> LENGTH: 30
<212> TYPE: DNA
<213> ORGANISM: Artificial Sequence
<220> FEATURE:
<223> OTHER INFORMATION: oligonucleotide

<400> SEQUENCE: 1
gcgtttaagc ttacatgatc tgcagagagg                                              30

<210> SEQ ID NO 2
<211> LENGTH: 42
<212> TYPE: DNA
<213> ORGANISM: Artificial Sequence
<220> FEATURE:
<223> OTHER INFORMATION: oligonucleotide

<400> SEQUENCE: 2
ggcggaaaga tcgccgtgta aaggttgggg taaacactcc gg                                42

<210> SEQ ID NO 3
<211> LENGTH: 48
<212> TYPE: DNA
<213> ORGANISM: Artificial Sequence
<220> FEATURE:
<223> OTHER INFORMATION: oligonucleotide

<400> SEQUENCE: 3
ctgtggacgt cggttggtgt tacgtttggt ttttctttga ggtttagg                          48

<210> SEQ ID NO 4
<211> LENGTH: 39
<212> TYPE: DNA
<213> ORGANISM: Artificial Sequence
<220> FEATURE:
<223> OTHER INFORMATION: oligonucleotide

<400> SEQUENCE: 4
ggctgggacc atgccggccg ccagccccct gatggggc                                     39

<210> SEQ ID NO 5
<211> LENGTH: 42
<212> TYPE: DNA
<213> ORGANISM: Artificial Sequence
<220> FEATURE:
<223> OTHER INFORMATION: oligonucleotide

<400> SEQUENCE: 5
ccggagtgtt tacccaacc tttacacggc gatctttccg cc                                 42

<210> SEQ ID NO 6
<211> LENGTH: 40
<212> TYPE: DNA
<213> ORGANISM: Artificial Sequence
<220> FEATURE:
<223> OTHER INFORMATION: oligonucleotide

<400> SEQUENCE: 6
ttggtagacg tccaatggaa gacgccaaaa taaagaaagg                                   40

<210> SEQ ID NO 7
<211> LENGTH: 39

```
<212> TYPE: DNA
<213> ORGANISM: Artificial Sequence
<220> FEATURE:
<223> OTHER INFORMATION: oligonucleotide

<400> SEQUENCE: 7
gcccccatca gggggctggc ggccggcatg gtcccagcc                    39

<210> SEQ ID NO 8
<211> LENGTH: 29
<212> TYPE: DNA
<213> ORGANISM: Artificial Sequence
<220> FEATURE:
<223> OTHER INFORMATION: oligonucleotide

<400> SEQUENCE: 8
ctcaagctct agagagattt gtgggtccc                               29

<210> SEQ ID NO 9
<211> LENGTH: 36
<212> TYPE: DNA
<213> ORGANISM: Artificial Sequence
<220> FEATURE:
<223> OTHER INFORMATION: oligonucleotide

<400> SEQUENCE: 9
gaagacgcca aaacataaa gaagggcccg gcgcca                        36

<210> SEQ ID NO 10
<211> LENGTH: 36
<212> TYPE: DNA
<213> ORGANISM: Artificial Sequence
<220> FEATURE:
<223> OTHER INFORMATION: oligonucleotide

<400> SEQUENCE: 10
tggcgccggg cccttcttta tgttttggc gtcttc                        36

<210> SEQ ID NO 11
<211> LENGTH: 30
<212> TYPE: DNA
<213> ORGANISM: Artificial Sequence
<220> FEATURE:
<223> OTHER INFORMATION: oligonucleotide

<400> SEQUENCE: 11
cctcttaggc catttcctgt tttttttttt                              30

<210> SEQ ID NO 12
<211> LENGTH: 30
<212> TYPE: DNA
<213> ORGANISM: Artificial Sequence
<220> FEATURE:
<223> OTHER INFORMATION: oligonucleotide

<400> SEQUENCE: 12
aaaaaaaaaa acaggaaatg gcctaagagg                              30

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
```

-continued

```
ccgagtgtag taaacattcc                                                   20

<210> SEQ ID NO 14
<211> LENGTH: 18
<212> TYPE: DNA
<213> ORGANISM: Artificial Sequence
<220> FEATURE:
<223> OTHER INFORMATION: oligonucleotide

<400> SEQUENCE: 14
ctcgcatgcc agagatcc                                                     18

<210> SEQ ID NO 15
<211> LENGTH: 22
<212> TYPE: DNA
<213> ORGANISM: Artificial Sequence
<220> FEATURE:
<223> OTHER INFORMATION: oligonucleotide

<400> SEQUENCE: 15
gatcttcgaa tgcatcgcgc gc                                                22

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
ggccttgact agagggtacc                                                   20

<210> SEQ ID NO 17
<211> LENGTH: 5860
<212> TYPE: DNA
<213> ORGANISM: viral

<400> SEQUENCE: 17
ggatccgctg tggaatgtgt gtcagttagg gtgtggaaag tccccaggct ccccagcagg       60
cagaagtatg caaagcatgc atctcaatta gtcagcaacc aggtgtggaa agtccccagg     120
ctccccagca ggcagaagta tgcaaagcat gcatctcaat tagtcagcaa ccatagtccc     180
gcccctaact ccgcccatcc cgcccctaac tccgcccagt tccgcccatt ctccgcccca     240
tggctgacta atttttttta tttatgcaga ggccgaggcc gcctcggcct ctgagctatt     300
ccagaagtag tgaggaggct ttttggagg cctaggcttt tgcaaaaagc ttacatgatc      360
tgcagagagg ccagtatcag cactctctgc agtcatgcgg ctcacggacc tttcacagct     420
agccgtgact agggctaaga tggagccacc attaaagaag aaggaaaag aaaggaaaaa      480 agaaggaaag aaaaaaaaaa aaaaaaaaaa ggaaaaaaaa aaaaaaaaag aaaaaaaaaa     540
aaaaaaaaaa aaaaaaaaaa aaaaaaaaaa aaaaaaaaaa aaacaggaaa tggcctaaga    600
ggccggagtg tttaccccaa cctttaaacg gcgatcttc cgcccttctt ggcctttatg      660
aggatctctc tgattttct tgcgtcgagt tttccggtaa gaccttcgg tacttcgtcc       720 acaaacacaa ctcctccgcg caacttttc gcggttgtta cttgactggc gacgtaatcc      780
acgatctctt tttccgtcat cgtctttccg tgctccaaaa caacaacggc ggcgggaagt     840
tcaccggcgt catcgtcggg aagacctgcg cacctgcgt cgaagatgtt ggggtgttgg      900
agcaagatgg attccaattc agcgggagcc acctgatagc ctttgtactt aatcagagac     960
ttcaggcggt caacgatgaa gaagtgttcg tcttcgtccc agtaagctat gtctccagaa   1020
```

```
tgtagccatc catccttgtc aatcaaggcg ttggtcgctt ccggattgtt tacataaccg    1080
gacataatca taggacctct cacacacagt tcgcctcttt gattaacgcc cagcgttttc    1140
ccggtatcca gatccacaac cttcgcttca aaaaatggaa caactttacc gaccgcgccc    1200
ggtttatcat cccctcggg tgtaatcaga atagctgatg tagtctcagt gagcccatat     1260
ccttgcctga tacctggcag atggaacctc ttggcaaccg cttccccgac ttccttagag    1320
aggggagcgc caccgaaagc aatttcgtgt aaattagata atcgtatt gtcaatcaga     1380 gtgcttttgg cgaagaagga aataggggtt ggcaccagca gcgcactttg aatcttgtaa    1440
tcctgaaggc tcctcagaaa cagctcttct tcaaatctat acattaagac gactcgaaat    1500
ccacatatca aatatccgag tgtagtaaac attccaaaac cgtgatggaa tggaacaaca    1560
cttaaaatcg cagtatccgg aatgatttga ttgccaaaaa taggatctct ggcatgcgag    1620
aatctcacgc aggcagttct atgaggcaga gcgacacctt taggcagacc agtagatcca    1680
gaggagttca tgatcagtgc aattgtcttg tccctatcga aggactctgg cacaaaatcg    1740
tattcattaa aaccgggagg tagatgagat gtgacgaacg tgtacatcga ctgaaatccc    1800
tggtaatccg ttttagaatc catgataata attttttgga tgattgggag cttttttgc     1860 acgttcaaaa ttttttgcaa ccccttttg gaaacgaaca ccacggtagg ctgcgaaatg     1920
cccatactgt tgagcaattc acgttcatta taaatgtcgt tcgcgggcgc aactgcaact    1980
ccgataaata acgcgcccaa caccggcata agaattgaa gagagttttc actgcatacg     2040
acgattctgt gatttgtatt cagcccatat cgtttcatag cttctgccaa ccgaacggac    2100
atttcgaagt actcagcgta agtgatgtcc acctcgatat gtgcatctgt aaaagcaatt    2160
gttccaggaa ccagggcgta tctcttcata gccttatgca gttgctctcc agcggttcca    2220
tcttccagcg gatagaatgg cgccgggcct ttctttatgt ttttggcgtc ttccatggga    2280
cgtcggttgg tgttacgttt ggttttctt tgaggtttag gattcgtgct catgatgcac     2340
ggtctacgag acctcccggg gcactcgcaa gcaccctatc aggcagtacc acaaggcctt    2400
tcgcgaccca acactactcg gctagcagtc ttgcggggc acgcccaaat ctccaggcat     2460 tgagcgggt tatccaagaa aggacccggt cgtcctggca attccggtgt actcaccggt     2520
tccgcagacc actatggctc tcccgggagg ggggtcctg gaggctgcac gacactcata     2580
ctaacgccat ggctagacgc ttctgcgtg aagacagtag ttcctcacag gggagtgatt     2640
catggtggag tgtcgccccc atcagggggc tggcggccgg catggtccca gcctcctcgc    2700
tggcgccggc tgggcaacat tccgagggga ccgtcccctc ggtaatggcg aatgggaccc    2760
acaaatctct ctagatacct aggtgagctc tcggtacctc gagaattcga acgcgtgatc    2820
agctgttcta tagtgtcacc taaatagctt cgaggtcgac ctcgaaactt gtttattgca    2880
gcttataatg gttacaaata aagcaatagc atcacaaatt tcacaaataa gcattttt      2940 tcactgcatt ctagttgtgg tttgtccaaa ctcatcaatg tatcttatca tgtctggatc    3000
cctcggagat ctgggcccat gcggccgcg atcgatgctc actcaaaggc ggtaatacgg     3060
ttatccacag aatcagggga taacgcagga agaacatgt gagcaaaagg ccagcaaaag     3120
gccaggaacc gtaaaaagc cgcgttgctg gcgttttcc ataggctccg ccccctgac       3180 gagcatcaca aaaatcgacg ctcaagtcag aggtggcgaa acccgacagg actataaaga    3240
taccaggcgt tttcccctgg aagctccctc gtgcgctctc ctgttccgac cctgccgctt    3300
accggatacc tgtccgcctt tctcccttcg ggaagcgtgg cgctttctca atgctcacgc    3360
```

-continued

```
tgtaggtatc tcagttcggt gtaggtcgtt cgctccaagc tgggctgtgt gcacgaaccc    3420
cccgttcagc ccgaccgctg cgccttatcc ggtaactatc gtcttgagtc caacccggta    3480
agacacgact tatcgccact ggcagcagcc actggtaaca ggattagcag agcgaggtat    3540
gtaggcggtg ctacagagtt cttgaagtgg tggcctaact acggctacac tagaaggaca    3600
gtatttggta tctgcgctct gctgaagcca gttaccttcg gaaaaagagt tggtagctct    3660
tgatccggca aacaaaccac cgctggtagc ggtggttttt ttgtttgcaa gcagcagatt    3720
acgcgcagaa aaaaggatc tcaagaagat cctttgatct tttctacggg gtctgacgct    3780
cagtggaacg aaaactcacg ttaagggatt ttggtcatga cattaaccta taaaaatagg    3840
cgtatcacga ggccctttcg tctcgcgcgt ttcggtgatg acggtgaaaa cctctgacac    3900
atgcagctcc cggagacggt cacagcttgt ctgtaagcgg atgccgggag cagacaagcc    3960
cgtcagggcg cgtcagcggg tgttggcggg tgtcggggct ggcttaacta tgcggcatca    4020
gagcagattg tactgagagt gcaccatatg cggtgtgaaa taccgcacag atgcgtaagg    4080
agaaaatacc gcatcaggcg acgcgccctg tagcggcgca ttaagcgcgg cgggtgtggt    4140
ggttacgcgc agcgtgaccg ctacacttgc cagcgcccta gcgcccgctc ctttcgcttt    4200
cttcccttcc tttctcgcca cgttcgccgg ctttccccgt caagctctaa atcgggggct    4260
ccctttaggg ttccgattta gagctttacg gcacctcgac cgcaaaaaac ttgatttggg    4320
tgatggttca cgtagtgggc catcgccctg atagacggtt tttcgccctt gacgttgga    4380 gtccacgttc tttaatagtg gactcttgtt ccaaactgga acaacactca accctatctc    4440
ggtctattct tttgatttat aagggatttt gccgatttcg gcctattggt taaaaaatga    4500
gctgatttaa caaatattta acgcgaattt taacaaaata ttaacgttta caatttccat    4560
tcgccattca ggctgcaact agatctagag tccgttacat aacttacggt aaatggcccg    4620
cctggctgac cgcccaacga cccccgccca ttgacgtcaa taatgacgta tgttcccata    4680
gtaacgccaa tagggacttt ccattgacgt caatgggtgg agtatttacg gtaaactgcc    4740
cacttggcag tacatcaagt gtatcatatg ccaagtacgc cccctattga cgtcaatgac    4800
ggtaaatggc ccgcctggca ttatgcccag tacatgacct tatgggactt tcctacttgg    4860
cagtacatct acgtattagt catcgctatt accatggtga tgcggttttg gcagtacatc    4920
aatgggcgtg gatagcggtt tgactcacgg ggatttccaa gtctccaccc cattgacgtc    4980
aatgggagtt tgttttggca ccaaaatcaa cgggactttc caaaatgtcg taacaactcc    5040
gccccattga cgcaaatggg cggtaggcgt gtacggtggg aggtctatat aagcagagct    5100
cgtttagtga accgtcagat cgcctggaga cgccatccac gctgttttga cctccataga    5160
agacaccggg accgatccag cctccgcggc cgggaacggt gcattggaac ggacctgcag    5220
cacgtgttga caattaatca tcggcatagt atatcggcat agtataatac gactcactat    5280
aggagggcca ccatggccaa gttgaccagt gccgttccgg tgctcaccgc gcgcgacgtc    5340
gccggagcgg tcgagttctg gaccgaccgg ctcgggttct cccggactt cgtgaggac    5400 gacttcgccg gtgtggtccg ggacgacgtg accctgttca cagcgcggt ccaggaccag    5460 gtggtgccgg acaacaccct ggcctgggtg tgggtgcgcg gctgacga gctgtacgcc    5520 gagtggtcgg aggtcgtgtc cacgaacttc cgggacgcct ccgggccggc catgaccgag    5580
atcggcgagc agccgtgggg gcgggagttc gccctgcgcg accgcgcgg caactgcgtg    5640 cacttcgtgg ccgaggagca ggactgaccg acgccgacca acaccgccgg tccgacggcg    5700
gcccacgggt cccaggggg tcgacctcga aacttgttta ttgcagctta taatggttac    5760
```

|  |  |
|---|---|
| aaataaagca atagcatcac aaatttcaca aataaagcat ttttttcact gcattctagt | 5820 |
| tgtggtttgt ccaaactcat caatgtatct tatcatgtct | 5860 |

<210> SEQ ID NO 18
<211> LENGTH: 2771
<212> TYPE: DNA
<213> ORGANISM: viral

<400> SEQUENCE: 18

|  |  |
|---|---|
| ggatccgctg tggaatgtgt gtcagttagg gtgtggaaag tccccaggct ccccagcagg | 60 |
| cagaagtatg caaagcatgc atctcaatta gtcagcaacc aggtgtggaa agtccccagg | 120 |
| ctccccagca ggcagaagta tgcaaagcat gcatctcaat tagtcagcaa ccatagtccc | 180 |
| gcccctaact ccgcccatcc cgcccctaac tccgcccagt tccgcccatt ctccgcccca | 240 |
| tggctgacta atttttttta tttatgcaga ggccgaggcc gcctcggcct ctgagctatt | 300 |
| ccagaagtag tgaggaggct ttttggagg cctaggcttt tgcaaaaagc ttacatgatc | 360 |
| tgcagagagg ccagtatcag cactctctgc agtcatgcgg ctcacggacc tttcacagct | 420 |
| agccgtgact agggctaaga tggagccacc attaaagaag gaaggaaaag aaaggaaaaa | 480 |
| agaaggaaag aaaaaaaaaa aaaaaaaaaa ggaaaaaaaa aaaaaaaaag aaaaaaaaaa | 540 |
| aaaaaaaaaa aaaaaaaaaa aaaaaaaaaa aaaaaaaaaa aaacaggaaa tggcctaaga | 600 |
| ggccggagtg tttaccccaa cctttaaacg gcgatctttc cgcccttctt ggcctttatg | 660 |
| aggatctctc tgattttttct tgcgtcgagt tttccggtaa gacctttcgg tacttcgtcc | 720 |
| acaaacacaa ctcctccgcg caacttttc gcggttgtta cttgactggc gacgtaatcc | 780 |
| acgatctctt tttccgtcat cgtctttccg tgctccaaaa caacaacggc ggcgggaagt | 840 |
| tcaccggcgt catcgtcggg aagacctgcg cacctgcgt cgaagatgtt ggggtgttgg | 900 |
| agcaagatgg attccaattc agcgggagcc acctgatagc ctttgtactt aatcagagac | 960 |
| ttcaggcggt caacgatgaa gaagtgttcg tcttcgtccc agtaagctat gtctccagaa | 1020 |
| tgtagccatc catccttgtc aatcaaggcg ttggtcgctt ccggattgtt acataaccg | 1080 |
| gacataatca taggacctct cacacacagt tcgcctcttt gattaacgcc cagcgttttc | 1140 |
| ccggtatcca gatccacaac cttcgcttca aaaatggaa caactttacc gaccgcgccc | 1200 |
| ggtttatcat cccctcgggg tgtaatcaga atagctgatg tagtctcagt gagcccatat | 1260 |
| ccttgcctga tacctggcag atggaacctc ttggcaaccg cttccccgac ttccttagag | 1320 |
| aggggagcgc caccagaagc aatttcgtgt aaattagata atcgtatttt gtcaatcaga | 1380 |
| gtgcttttgg cgaagaagga gaatagggtt ggcaccagca gcgcactttg aatcttgtaa | 1440 |
| tcctgaaggc tcctcagaaa cagctcttct tcaaatctat acattaagac gactcgaaat | 1500 |
| ccacatatca aatatccgag tgtagtaaac attccaaaac cgtgatggaa tggaacaaca | 1560 |
| cttaaaatcg cagtatccgg aatgatttga ttgccaaaaa taggatctct ggcatgcgag | 1620 |
| aatctcacgc aggcagttct atgaggcaga gcgacacctt taggcagacc agtagatcca | 1680 |
| gaggagttca tgatcagtgc aattgtcttg tccctatcga aggactctgg cacaaaatcg | 1740 |
| tattcattaa aaccgggagg tagatgagat gtgacgaacg tgtacatcga ctgaaatccc | 1800 |
| tggtaatccg ttttagaatc catgataata attttttgga tgattgggag cttttttttgc | 1860 |
| acgttcaaaa tttttttgcaa ccccttttg gaaacgaaca ccacggtagg ctgcgaaatg | 1920 |
| cccatactgt tgagcaattc acgttcatta taaatgtcgt tcgcgggcgc aactgcaact | 1980 |

-continued

| | |
|---|---|
| ccgataaata acgcgcccaa caccggcata aagaattgaa gagagttttc actgcatacg | 2040 |
| acgattctgt gatttgtatt cagcccatat cgtttcatag cttctgccaa ccgaacggac | 2100 |
| atttcgaagt actcagcgta agtgatgtcc acctcgatat gtgcatctgt aaaagcaatt | 2160 |
| gttccaggaa ccagggcgta tctcttcata gccttatgca gttgctctcc agcggttcca | 2220 |
| tcttccagcg gatagaatgg cgccgggcct ttctttatgt ttttggcgtc ttccatggga | 2280 |
| cgtcggttgg tgttacgttt ggttttcctt tgaggtttag gattcgtgct catgatgcac | 2340 |
| ggtctacgag acctcccggg gcactcgcaa gcaccctatc aggcagtacc acaaggcctt | 2400 |
| tcgcgaccca acactactcg gctagcagtc ttgcggggc acgcccaaat ctccaggcat | 2460 |
| tgagcgggt tatccaagaa aggacccggt cgtcctggca attccggtgt actcaccggt | 2520 |
| tccgcagacc actatggctc tcccgggagg ggggtcctg gaggctgcac gacactcata | 2580 |
| ctaacgccat ggctagacgc tttctgcgtg aagacagtag ttcctcacag gggagtgatt | 2640 |
| catggtggag tgtcgccccc atcagggggc tggcggccgg catggtccca gcctcctcgc | 2700 |
| tggcgccggc tgggcaacat tccgagggga ccgtcccctc ggtaatggcg aatgggaccc | 2760 |
| acaaatctct c | 2771 |

<210> SEQ ID NO 19
<211> LENGTH: 2674
<212> TYPE: DNA
<213> ORGANISM: viral

<400> SEQUENCE: 19

| | |
|---|---|
| ggatccgctg tggaatgtgt gtcagttagg gtgtggaaag tccccaggct ccccagcagg | 60 |
| cagaagtatg caaagcatgc atctcaatta gtcagcaacc aggtgtggaa agtccccagg | 120 |
| ctccccagca ggcagaagta tgcaaagcat gcatctcaat tagtcagcaa ccatagtccc | 180 |
| gcccctaact ccgcccatcc cgcccctaac tccgcccagt tccgcccatt ctccgcccca | 240 |
| tggctgacta attttttta tttatgcaga ggccgaggcc gcctcggcct ctgagctatt | 300 |
| ccagaagtag tgaggaggct ttttggagg cctaggcttt tgcaaaaagc ttacatgatc | 360 |
| tgcagagagg ccagtatcag cactctctgc agtcatgcgg ctcacggacc tttcacagct | 420 |
| agccgtgact agggctaaga tggagccacc attaaagaag gaaggaaaag aaaggaaaaa | 480 |
| agaaggaaag aaaaaaaaaa aaaaaaaaaa ggaaaaaaaa aaaaaaaaag aaaaaaaaaa | 540 |
| aaaaaaaaaa aaaaaaaaaa aaaaaaaaa aaaaaaaaaa aaacaggaaa tggcctaaga | 600 |
| ggccggagtg tttaccccaa cctttaaacg gcgatctttc cgcccttctt ggcctttatg | 660 |
| aggatctctc tgattttct tgcgtcgagt tttccggtaa gacctttcgg tacttcgtcc | 720 |
| acaaacacaa ctcctccgcg caacttttc gcggttgtta cttgactggc gacgtaatcc | 780 |
| acgatctctt tttccgtcat cgtctttccg tgctccaaaa caacaacggc ggcgggaagt | 840 |
| tcaccggcgt catcgtcggg aagacctgcg acacctgcgt cgaagatgtt ggggtgttgg | 900 |
| agcaagatgg attccaattc agcgggagcc acctgatagc ctttgtactt aatcagagac | 960 |
| ttcaggcggt caacgatgaa gaagtgttcg tcttcgtccc agtaagctat gtctccagaa | 1020 |
| tgtagccatc catccttgtc aatcaaggcg ttggtcgctt ccggattgtt tacataaccg | 1080 |
| gacataatca taggacctct cacacacagt tcgcctcttt gattaacgcc cagcgttttc | 1140 |
| ccggtatcca gatccacaac cttcgcttca aaaatggaa caactttacc gaccgcgccc | 1200 |
| ggtttatcat cccctcgggg tgtaatcaga atagctgatg tagtctcagt gagcccatat | 1260 |
| ccttgcctga tacctggcag atggaacctc ttggcaaccg cttccccgac ttccttagag | 1320 |

```
agggagcgc caccagaagc aatttcgtgt aaattagata aatcgtattt gtcaatcaga    1380
gtgcttttgg cgaagaagga gaataggggtt ggcaccagca gcgcactttg aatcttgtaa   1440
tcctgaaggc tcctcagaaa cagctcttct tcaaatctat acattaagac gactcgaaat   1500
ccacatatca aatatccgag tgtagtaaac attccaaaac cgtgatggaa tggaacaaca   1560
cttaaaatcg cagtatccgg aatgatttga ttgccaaaaa taggatctct ggcatgcgag   1620
aatctcacgc aggcagttct atgaggcaga gcgacaccnt taggcagacc agtagatcca   1680
gaggagttca tgatcagtgc aattgtcttg tccctatcga aggactctgg cacaaaatcg   1740
tattcattaa aaccgggagg tagatgagat gtgacgaacg tgtacatcga ctgaaatccc   1800
tggtaatccg ttttagaatc catgataata attttttgga tgattgggag cttttttgc    1860 acgttcaaaa ttttttgcaa cccctttttg gaaacgaaca ccacggtagg ctgcgaaatg   1920
cccatactgt tgagcaattc acgttcatta taaatgtcgt tcgcgggcgc aactgcaact   1980
ccgataaata acgcgcccaa caccggcata aagaattgaa gagagttttc actgcatacg   2040
acgattctgt gatttgtatt cagcccatat cgtttcatag cttctgccaa ccgaacggac   2100
atttcgaagt actcagcgta agtgatgtcc acctcgatat gtgcatctgt aaaagcaatt   2160
gttccaggaa ccaggcgta tctcttcata gccttatgca gttgctctcc agcggttcca   2220
tcttccagcg gatagaatgg cgccgggcct ttctttatgt ttttggcgtc ttccatggga   2280
cgtcggttgg tgttacgttt ggtttttctt tgaggtttag gattcgtgct catgatgcac   2340
ggtctacgag acctcccggg gcactcgcaa gcaccctatc aggcagtacc acaaggcctt   2400
tcgcgaccca acactactcg gctagcagtc ttgcgggggc acgcccaaat ctccaggcat   2460 tgagcgggt tatccaagaa aggacccggt cgtcctggca attccggtgt actcaccggt   2520
tccgcagacc actatggctc tcccgggagg ggggtcctg gaggctgcac gacactcata   2580
ctaacgccat ggctagacgc tttctgcgtg aagacgtag ttcctcacag gggagtgatt   2640
catggtggag tgtcgccccc atcaggggc tggc                             2674
```

<210> SEQ ID NO 20
<211> LENGTH: 2327
<212> TYPE: DNA
<213> ORGANISM: viral

<400> SEQUENCE: 20

```
agcttacatg atctgcagag aggccagtat cagcactctc tgcagtcatg cggctcacgg    60
accttccaca gctagccgtg actagggcta agatggagcc accattaaag aaggaaggaa   120
aagaaaggaa aaagaaggaa aagaaaaaaa aaaaaaaaaa aaaggaaaaa aaaaaaaaaa   180
aagaaaaaaa aaaaaaaaaa aaaaaaaaaa aaaaaaaaaa aaaaaaaaaa aaaaaacagg   240
aaatggccta agaggccgga gtgtttaccc caacctttaa acggcgatct ttccgcccnt   300
cttggccttt atgaggatct ctctgatttt tcttgcgtcg agttttccgg taagaccttt   360
cggtacttcg tccacaaaca caactcctcc gcgcaacttt tcgcggttg ttacttgact    420 ggcgacgtaa tccacgatct ctttttccgt catcgtcttt ccgtgctcca aaacaacaac   480
ggcggcggga agttcaccgg cgtcatcgtc gggaagacct cgacacctg cgtcgaagat    540 gttgggggtgt tggagcaaga tggattccaa ttcagcggga gccacctgat agcctttgta   600
cttaatcaga gacttcaggc ggtcaacgat gaagaagtgt tcgtcttcgt cccagtaagc   660
tatgtctcca gaatgtagcc atccatcctt gtcaatcaag gcgttggtcg cttccggatt   720
```

-continued

```
gtttacataa ccggacataa tcataggacc tctcacacac agttcgcctc tttgattaac      780
gcccagcgtt ttcccggtat ccagatccac aaccttcgct tcaaaaaatg gaacaacttt      840
accgaccgcg cccggtttat catccccctc gggtgtaatc agaatagctg atgtagtctc      900
agtgagccca tatccttgcc tgatacctgg cagatggaac ctcttggcaa ccgcttcccc      960
gacttcctta gagaggggag cgccaccaga agcaatttcg tgtaaattag ataaatcgta     1020
tttgtcaatc agagtgcttt tggcgaagaa ggagaatagg gttggcacca gcagcgcact     1080
ttgaatcttg taatcctgaa ggctcctcag aaacagctct tcttcaaatc tatacattaa     1140
gacgactcga aatccacata tcaaatatcc gagtgtagta aacattccaa aaccgtgatg     1200
gaatggaaca acacttaaaa tcgcagtatc cggaatgatt tgattgccaa aaataggatc     1260
tctggcatgc gagaatctca cgcaggcagt tctatgaggc agagcgacac ctttaggcag     1320
accagtagat ccagaggagt tcatgatcag tgcaattgtc ttgtccctat cgaaggactc     1380
tggcacaaaa tcgtattcat taaaaccggg aggtagatga gatgtgacga acgtgtacat     1440
cgactgaaat ccctggtaat ccgttttaga atccatgata ataattttt ggatgattgg     1500 gagcttttt tgcacgttca aaattttttg caaccccttt ttggaaacga acaccacggt     1560
aggctgcgaa atgcccatac tgttgagcaa ttcacgttca ttataaatgt cgttcgcggg     1620
cgcaactgca actccgataa ataacgcgcc caacaccggc ataaagaatt gaagagagtt     1680
ttcactgcat acgacgattc tgtgatttgt attcagccca tatcgtttca tagcttctgc     1740
caaccgaacg gacatttcga agtactcagc gtaagtgatg tccacctcga tatgtgcatc     1800
tgtaaaagca attgttccag gaaccagggc gtatctcttc atagccttat gcagttgctc     1860
tccagcggtt ccatcttcca gcggatagaa tggcgccggg cctttcttta tgttttttggc    1920 gtcttccatg ggacgtcggt tggtgttacg tttggttttt ctttgaggtt taggattcgt     1980
gctcatgatg cacggtctac gagacctccc ggggcactcg caagcaccct atcaggcagt     2040
accacaaggc ctttcgcgac ccaacactac tcggctagca gtcttgcggg ggcacgccca     2100
aatctccagg cattgagcgg ggttatccaa gaaaggaccc ggtcgtcctg gcaattccgg     2160
tgtactcacc ggttccgcag accactatgg ctctcccggg aggggggtc ctggaggctg      2220 cacgacactc atactaacgc catggctaga cgctttctgc gtgaagacag tagttcctca     2280
caggggagtg attcatggtg gagtgtcgcc cccatcaggg ggctggc                   2327
```